United States Patent [19]

Murphy et al.

[11] Patent Number: 4,983,418
[45] Date of Patent: Jan. 8, 1991

[54] SILICONE HAIRSPRAY COMPOSITIONS

[75] Inventors: Carolyn S. Murphy, Mason, Ohio; Mark R. Prausnitz, Somerville, Mass.

[73] Assignee: The Procter & Gamble Company, Cincinnati, Ohio

[21] Appl. No.: 429,895

[22] Filed: Oct. 31, 1989

[51] Int. Cl.$^5$ ............................................. A61K 7/00
[52] U.S. Cl. .................................. 424/47; 424/70; 424/71
[58] Field of Search ........................... 424/47, 70, 71

[56] References Cited

U.S. PATENT DOCUMENTS

| | | | |
|---|---|---|---|
| 2,643,375 | 6/1953 | Gant | 132/7 |
| 3,325,439 | 6/1967 | Steinbach | 260/32.8 |
| 3,681,122 | 8/1972 | Domicone et al. | 117/124 |
| 3,928,558 | 12/1975 | Chessmen et al. | 424/47 |
| 3,957,970 | 5/1976 | Korkis | 424/70 |
| 3,964,500 | 6/1976 | Drakoff | 132/7 |
| 4,174,386 | 11/1979 | Spitzer et al. | 424/47 |
| 4,221,688 | 9/1980 | Johnson et al. | 260/29.2 |
| 4,235,873 | 11/1980 | Packman | 424/47 |
| 4,344,763 | 8/1982 | Tolgyesi et al. | 8/127.51 |
| 4,364,837 | 12/1982 | Pader | 252/173 |
| 4,387,090 | 6/1983 | Bolich, Jr. | 424/70 |
| 4,450,152 | 5/1984 | Ona et al. | 424/70 |
| 4,472,375 | 9/1984 | Bolich, Jr. et al. | 424/70 |
| 4,487,883 | 12/1984 | Homan | 524/792 |
| 4,502,889 | 3/1985 | Kurita | 106/287.12 |
| 4,515,784 | 5/1985 | Bogardus et al. | 514/63 |
| 4,529,586 | 7/1985 | DeMarco et al. | 424/70 |
| 4,559,227 | 12/1985 | Chandra et al. | 424/70 |
| 4,704,272 | 11/1987 | Oh et al. | 424/70 |
| 4,728,457 | 3/1988 | Fieler et al. | 252/174.15 |
| 4,741,855 | 5/1988 | Grote et al. | 252/142 |
| 4,788,006 | 11/1988 | Bolich, Jr. et al. | 252/550 |
| 4,834,968 | 5/1989 | Bolich, Jr. | 424/47 |
| 4,842,850 | 6/1989 | Vu | 424/70 |
| 4,871,529 | 10/1989 | Sramek | 424/47 |
| 4,902,499 | 2/1990 | Bolish | 424/47 |

FOREIGN PATENT DOCUMENTS

| | | |
|---|---|---|
| 155806 | 9/1985 | European Pat. Off. |
| 56-022716 | 3/1981 | Japan . |
| 56-129300 | 10/1981 | Japan . |
| 57-162768 | 10/1982 | Japan . |
| 58-177909 | 10/1983 | Japan . |
| 61-044972 | 3/1986 | Japan . |
| 61-158914 | 7/1986 | Japan . |
| 61-161214 | 7/1986 | Japan . |
| 61-195138 | 8/1986 | Japan . |
| 2170216A | 7/1986 | United Kingdom . |

OTHER PUBLICATIONS

Chemical Abstracts, vol. 94, No. 2, May 1981, p. 373, column 1, Abstract No. 162601q.
Chemical Abstracts, vol. 97, No. 23, Dec. 1982, p. 324, column 1, Abstract No. 203098p.
U.S. Ser. No. 031,480, Bolich, Jr. et al., filed Mar. 27, 1987.
U.S. Ser. No. 112,975, Cobb et al., filed Oct 23, 1987.
U.S. Ser. No. 427,213, Maksimoski et al., filed Oct. 31, 1989.
U.S. Ser. No. 429,894, Murphy et al., filed Oct. 31, 1989.

Primary Examiner—Merrell C. Cashion, Jr.
Assistant Examiner—P. L. Prater
Attorney, Agent, or Firm—Gretchen R. Hatfield; Steven J. Goldstein

[57] ABSTRACT

Silicone hairspray compositions which give hair volume and hold but with a soft feel are disclosed. These compositions comprise from about 0.05% to about 10.0% of a silicone gum; from about 0.05% to about 7.5% of a dispersing aid for the silicone gum which may be a surfactant emulsifier or a hydrophobically-modified clay suspending/anti-agglomerating agent; and a volatile carrier, such as ethanol.

33 Claims, No Drawings

SILICONE HAIRSPRAY COMPOSITIONS

TECHNICAL FIELD

The present invention relates to silicone gum-containing hairspray compositions which provide improved hair conditioning and style volume and hold benefits. Agglomeration of the silicone gum is prevented by inclusion in the composition of a dispersing aid for the gum which may be a surfactant emulsifier or a hydrophobically-modified clay which acts as a suspending-/anti-agglomerating agent.

BACKGROUND OF THE INVENTION

The desire to have hair retain a particular shape is widely held. The two methodologies of accomplishing this are permanent chemical alteration of the hair or temporary alteration. A temporary alteration is one which can be removed by water or by shampooing. This has generally been accomplished by means of the application of a composition to dampened hair after shampooing and/or conditioning or to dry styled hair. The materials used to provide setting benefits have generally been resins or gums and have been applied in the form of mousses, gels, lotions, or sprays. Many people desire a high level of style retention such as that provided by a typical hair-spray composition without the negative impact that these materials generally have on dry hair properties, particularly hair manageability and hair feel.

Silicones in various hair care compositions have been disclosed in a large number of different publications, including U.S. Pat. No. 3,964,500. Drakoff, issued June 22, 1976; U.S. Pat. No. 4,364,837, Pader, issued Dec. 21, 1981; U.S. Pat. No. 4,341,799, Good, issued July 27, 1982; U.S. Pat. No. 4,465,619, Boskamp, issued Aug. 14, 1984; U.S. Pat. No. 4,515,784. Bogartus, issued May 7, 1985; U.S. Pat. No. 4,387,090, Bolich, issued June 7, 1983; and U.S. Pat. No. 4,529,586, DeMarco et al., issued July 16, 1985.

Silicone fluids in aqueous-based hair mousse compositions are disclosed in U.S. Pat. No. 4,764,363. Bolich, Jr., issued Aug. 16, 1988. Silicone gums in aqueous-based hair mousse compositions are disclosed in U.S. Pat. No. 4,834,968, Bolich, Jr. et al., issued May 30, 1989.

Ser. No. 274,218, Maksimoski and Murphy, filed Nov. 21, 1988, discloses hair care compositions comprising certain silicone gums having dispersed therein certain particulate materials, which are not solubilized in the composition, to provide increased hair volume benefits and style retention. The compositions provide these benefits to the hair without negatively affecting dry hair properties such as ease of combing.

This is surprising since other silicone materials which have been typically used in hair care compositions as conditioners have decreased perceived hair volume and hurt style retention, and the resins and gums used frequently for style retention have generally hurt dry hair properties such as combing. Furthermore, hair styling polymers traditionally used in hair styling compositions tend to leave hair feeling stiff and sticky.

Though silicone gums have traditionally been difficult to formulate in typical hair spray compositions, comprising, e.g., an ethanol solvent, a method has now been discovered to make such formulations possible. This method comprises using a dispersing aid for the gum which can comprise either a surfactant emulsifier or a hydrophobically-modified clay as a dispersing/anti-agglomerating agent.

The hydrophobically modified clay materials have been used in the past as suspending agents for personal care compositions containing particulate materials. For example, EPO Patent Application No. 0028853, Beckmeyer et al., published May 20, 1981, discloses antiperspirant compositions comprising particulate antiperspirant salts, silicone fluids, and bulking/suspending agents which may be hydrophobically-modified clays. See also, U.S. Pat. No. 4,840,786, Johnson et al, issued June 20, 1989. U.S. Pat. No. 4,152,416, Spitzer et al., issued May 1, 1979, discloses antiperspirant compositions comprising antiperspirant salts, silicone gums, and bulking agents which may be colloidal silica or hydrophobic clays.

It is an object of the present invention to formulate hair spray compositions which provide a look of increased hair volume.

It is also an object of the present invention to formulate hair spray compositions which provide good style retention.

It is a further object of the present invention to formulate hair spray compositions containing silicone gums which provide good hair conditioning, and leave hair feeling soft.

These and other objects will become readily apparent from the detailed description which follows.

Unless otherwise indicated, all percentages and ratios herein are by weight.

SUMMARY OF THE INVENTION

The present invention relates to hair spray compositions comprising from about 0.05% to about 10% of a silicone gum; from about 0.05% to about 7.5% of a dispersing aid which may be a surfactant emulsifier or a hydrophobically-modified clay suspending/anti-agglomerating agent; and a volatile carrier.

DETAILED DESCRIPTION OF THE INVENTION

The essential as well as optional components are described below.

Silicone Gum

The compositions of the present invention contain, as an essential component, a silicone gum which when applied to hair imparts style retention and conditioning benefits.

Silicone liquids or fluids are not desirably used in hairspray compositions. Because these materials flow so readily they tend to completely coat the hair shafts and over-condition the hair. That is, they tend to leave the hair feeling too soft, almost slimy. Clearly this goes against the objective desired in using a hairspray, increased hair volume and style hold.

Among the silicone gums which are useful in the present invention are those which have complex viscosities of at least about 100,000 centistoke (CSTK) and up to about 300,000,000 CSTK and, preferably from about 1,000,000 CSTK to about 20,000,000 CSTK, where complex viscosity is measured by subjecting a sample to oscillatory shear at a fixed frequency of 0.1 rad/sec at 25.C using a Rheometric Fluids Spectrometer® measuring films having a thickness of about 1 millimeter. The resulting viscous and elastic force responses are combined to determine the complex modulus which is divided by the imposed frequency to compute the complex viscosity.

Silicone gums useful in the present invention include, but are not limited to, polydimethyl siloxane gums.

Preferred silicone gums for use in the present invention are materials which provide both style retention and conditioning benefits to the hair. These silicone gums are rigid silicone gums. Use of these materials will minimize the over-conditioning problem seen with silicone fluids and less rigid silicone gums.

Some examples of such materials include, by are not limited to, filler reinforced polydimethylsiloxane gums including those having end groups such as hydroxyl; cross linked siloxanes, such as organic substituted silicone elastomers, organic substituted siloxane gums, including those having end groups such as hydroxyl; resin reinforced siloxanes; and cross linked siloxane polymers.

By rigid silicone gums is meant those silicone materials which have complex viscosities of at least $2 \times 10^5$ poise (P), preferably about $1 \times 10^7$ poise.

A preferred silicone gum useful in the present compositions is a diphenyl-dimethyl polysiloxane gum having a molecular weight of at least about 500,000, and must be diphenyl substituted to the extent of 3% or more, preferably at least about 5%.

The silicone gums may also be filler reinforced to provide additional rigidity. Silica is a preferred filler. Fumed silica is most preferred. It has been found that its smaller particle size provides greater rigidity to the gum. Generally, such reinforced gums will comprise up to about 15% to about 20% silica.

Silicone elastomers useful in the hairspray compositions of the present invention are the materials described in U.S. Pat. No. 4,221,688, Johnson et al., issued Sept. 9, 1980, incorporated herein by reference. The actual material described in the patent and what can be put into the present compositions is an aqueous emulsion which dries to form an elastomer upon removal of the water.

The silicone emulsion has a continuous water phase in which there is a dispersed phase which comprises an anionically stabilized hydroxylated polyorganosiloxane, a colloidal silica and a catalyst. The pH of the emulsion should be in the range of from about 9 to about 11.5, preferably from about 10.5 to about 11.2. The solids content of the emulsion is generally from about 20% to about 60%, preferably from about 30% to about 50%. The amount of colloidal silica present for each 100 parts by weight of the polydiorganosiloxane is from 1 to 150 parts. On the same basis the amount of diorganotindicarboxylate (e.g., dioctyl tindilaurate) catalyst is from 0.1 to 2 parts. The elastomer emulsion is used in an amount of from about 0.1% to about 5%, preferably from about 0.5% to about 4%, of the total composition.

Silicone resins may also be used in the present hairspray compositions. These materials are silicone polymers with a high degree of crosslinking introduced through the use of trifunctional and tetrafunctional silanes. Typical silanes used in the manufacture of resins are monomethyl, dimethyl, monophenyl, diphenyl, methylphenyl, monovinyl, and methylvinyl chlorosilanes, together with tetrachlorosilane. A preferred resin is provided as a solution in toluene which is stripped prior to the resin's use.

Other rigid silicone gums of use herein are those siloxanes which have been sparingly crosslinked but are still soluble in solvents such as cyclomethicone. Precursers for the rigid material can be any high molecular weight polydimethyl siloxanes, polydimethyl siloxanes containing vinyl groups and other siloxanes. Methods of crosslinking include heat curing with organic peroxides such as dibenzoyl peroxide and di-t-butyl peroxide, heat vulcanization with sulfur, and high-energy radiation.

The silicone gum comprises from about 0.05% to about 10%, preferably from about 0.05% to about 7%, of the hair spray composition.

The compositions of the present invention preferably comprise a volatile silicone solvent, or mixtures thereof, for the gum. The volatile silicone solvent, if present, is at a level of from about 0.01% to about 10%, preferably from about 0.05% to about 5.0%, of the composition. The silicone solvent allows for easier and more even dispersion of the silicone gum in the hair spray composition. The term "volatile" as used herein means that the material has a measurable vapor pressure.

The preferred volatile silicone solvents have a boiling point between about 99° C. and about 260° C. and have a solubility in water of less than about 0.1%. The degree of substitution on the siloxane (higher substitution, lower solubility) obviously affects the polymer's solubility and must be taken into account by the formulator. The silicones may be either cyclic or linear polydimethyl siloxanes. The number of silicon atoms in the cyclic silicones is about 3 to about 7, most preferably 4 or 5. The general formula for the cyclic silicones is:

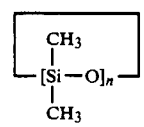

wherein $n=3-7$. Viscosities are generally less than about 10 centipoise (cP) at 25° C.

Linear polydimethyl siloxanes useful in the present invention generally have viscosities of less than about 5cP at 25° C. The linear volatile silicones contain from about 3 to about 9 silicone atoms and have the general formula:

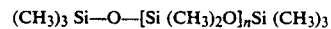

wherein $n=1-7$.

Silicones of the above-described types are widely available e.g., from Dow Corning as 344, 345 and 200 fluids; Union Carbide as Silicone 7202 and 7158; and Stauffer Chemical as SWS-03314.

The preferred volatile silicone solvent of the present invention is cyclomethicone available from G. E. Silicones. It is present in the compositions of the present invention at from about 0.05% to about 5.0%.

The volatile silicone solvent is preferably combined with the silicone gum in several steps to lower the viscosity of the gum. Any conventional means for mixing the two may be utilized.

DISPERSING AID

The hairspray compositions of the present invention require a dispersing aid for the silicone gum to disperse the silicone gum in the hairspray composition. Without a dispersing aid, incorporation of a silicone gum into a hairspray composition is essentially impossible. Though silicone gum can be finely dispersed in hairspray solvents such as ethanol, it tends to precipitate out of solution over time and form a solid mass at the bottom of the container. This solid mass is un-redispersible in the ethanol solvent upon agitation.

Surfactant Emulsifier

The dispersing agent of the present compositions can be a surfactant emulsifier. Useful surfactant emulsifier materials include anionic, nonionic, and cationic surfactant materials. Preferably, more than one emulsifier is used. Generally co-surfactant emulsifier systems are used, for example, an anionic surfactant plus a nonionic surfactant or a cationic surfactant plus a nonionic surfactant. Generally combinations of anionic and cationic surfactants will not provide the appropriate emulsifying benefit. The specific materials to be used and their respective levels should be chosen so that a microemulsion of the silicone gum in the hairspray composition can be formed. This microemulsion of the silicone gum in the hairspray solvent will remain stable over time if the emulsifier is appropriately chosen. One example of a particularly preferred emulsifying system comprises a combination of lauramine oxide and cocamide DEA.

The surfactant emulsifier, if used as the dispersing aid in the present hairspray compositions, is present at a level of from about 0.25% to about 7.5%.

Hydrophobically-treated Clay

The dispersing agent may alternatively comprise a hydrophobically-treated clay which acts as a suspending/anti-agglomerating agent in the hairspray composition. Though hair spray compositions formulated with these clay materials will still separate into two phases (a volatile carrier phase and a silicone gum phase) over time, the presence of the clay materials allows for redispersion of the silicone gum in the volatile carrier with a gentle shake of the container.

The suspending/anti-agglomerating agents useful herein include hydrophobically-treated montmorillonite clays, e.g., bentonites and hectorites. Untreated clays will not provide the same suspending/anti-agglomerating benefits in the present invention. The hectorite and bentonite hydrophobically-treated clay minerals of the instant compositions can be described as expandable (swellable), three-layer clays, in which a sheet of aluminum/oxygen atoms or magnesium/oxygen atoms lies between two layers of silicone/oxygen atoms, i.e., aluminosilicates and magnesium silicates, having an ion exchange capacity of at least about 50 meq/100 g of clay, and preferably at least about 60 meq/100 g of clay. The term "expandable" as used to describe clays relates to the ability of the layered clay structure to be swollen or expanded on contact with water. Such hectorite and bentonite clays are described in Grim, *Clay Mineralogy* (2nd. Ed.) pp. 77–79 (1968), and in Van Olphen, *An Introduction to Clay Colloid Chemistry*, (2nd Ed.) pp 64–76 (1977), both of which are incorporated by reference herein.

The clay minerals employed in the compositions of the instant invention contain exchangeable cations including, but not limited to, protons, sodium ions, potassium ions, calcium ions, magnesium ions, lithium ions, and the like.

It is customary to distinguish between clays on the basis of one cation predominantly or exclusively absorbed. For example, a sodium clay is one in which the absorbed cation is predominantly sodium. As used herein, the term clay, such as a hectorite clay, includes all the various exchangeable cation variants of that clay, e.g., sodium hectorite, potassium hectorite, lithium hectorite, magnesium hectorite, calcium hectorite, etc.

The clay minerals employed in the compositions of the instant invention are made hydrophobic by treating them with a cationic surfactant material. A preferred cationic surfactant is a quaternary ammonium cationic surfactant. A particularly preferred cationic surfactant is ditallow dimethyl ammonium chloride (e.g., quaternium-18).

Several of these hydrophobically-treated or hydrophobically-modified clay agents are commercially available. They include, for example, quaternium-18-bentonite, sold under the trade names Bentone-34 ® by NL chemicals and Tixogel VP ® by United Catalysts; quaternium-18-hectorite, sold under the tradename Bentone-38 ® by NL Chemicals; stearalkonium bentonite, sold under the tradename Tixogel-VZ ® by United Catalysts; and stearalkonium hectorite, sold under the trade name Bentone-27 ®by NL Chemicals.

If a hydrophobically-modified clay is used as a dispersing aid in the hairspray compositions of the present invention, it is present at a level of from about 0.05% to about 5.0%, preferably from about 0.05% to about 2.0%, by weight of the hairspray composition.

A small amount of water is required in the hairspray compositions of the present invention to activate the clay agent. Generally this requirement can be met by using a 190-proof ethanol solvent for the system. Alternatively, a small amount of water can be added to the hair spray composition.

An additional dispersing aid may be added to the hairspray compositions of the present invention to make redispersion of the silicone gum after phase separation easier. Dimethicone copolyol is a one such useful material. It may be added to the present hairspray compositions at a level of from about 0.01% to about 5%.

Volatile Carrier

The present hairspray compositions also comprise a volatile carrier system. This can comprise any of those conventionally used in resin hairspray formulations, preferably a $C_1-C_6$ alkanol, most preferably ethanol. This component "carries" the silicone gum to the hair then volatilizes, leaving the particulate containing gum behind on the hair to provide hair conditioning, hair volumizing benefits, and hairstyling hold. The carrier is present in the hairspray composition at from about 20% to about 95%, preferably from about 35% to about 95% by weight of the composition. Water can also be used to substitute for part of the volatile carrier component.

Hair Hold Resin

An additional component, that is preferably used in the present hairspray compositions, is a hair setting polymer. Any polymer soluble or dispersible in the volatile carrier or solvent phase may be used. Solubility/dispersibility is determined at ambient conditions (e.g., temperature about 25 C and atmospheric pressure). Suitable types of polymers include anionic, nonionic, amphoteric and cationic polymer materials. Specific polymers include polyvinylpyrrolidone (PVP), copolymers of (PVP) and methylmethacrylate, copolymers of PVP and vinylacetate (VA), polyvinyl alcohol (PVA), copolymers of PVA and crotonic acid, copolymers of PVA and maleic anhydride, hydroxypropyl cellulose, hydroxypropyl guar gum, sodium polystyrene sulfonate, PVP/ethylmethacrylate/methacrylic acid terpolymer, vinyl acetate/crotonic acid/vinyl neodecanoate copolymer, octylacrylamide/acrylates copolymer, monoethyl ester of poly(methyl vinyl ether-maleic acid), and octylacrylamide/acrylate/-butylaminoethyl methacrylate copolymers. Mixtures of polymers may also be used. PVP and PVP copolymers with other monomers are preferred. The most preferred resins for use in the present hairsprays are copolymers of polyvinyl pyrrolidone and vinyl acetate.

With certain of the polymers it may be necessary to neutralize some acidic groups to promote solubility/dispersibility (e.g., PVA/crotonic acid). Examples of suitable neutralizing agents include 2-amino-2-methyl-1,3-propanediol (AMPD); 2-amino2-ethyl-1,3-propanediol (AEPD); 2-amino-2-methyl-1-propanol (AMP); 2-amino-1-butanol (AB); monoethanolamine (MEA); di-ethanolamine (DEA); triethanolamine (TEA); monoisopropanolamine (MIPA); diisopropanol-amine (DIPA); triisopropanolamine (TIPA); and dimethyl stearamine (DMS).

When present the polymer(s) is used at a level of from about 0.25% to about 20%, preferably from about 1% to about 20%, of the total composition. The mass average molecular weight of the polymer is not critical, but is generally in the range of from about 2,000 to about 2,000,000.

These various components provide the user of the present compositions with a hairspray which after application provides hair styling hold, but with a softer feel to hair than traditional hair spray products provide.

Propellant

The present hairspray compositions may be formulated in aerosol or non-aerosol forms. If an aerosol hairspray is desired, a propellant must be included in the composition. This agent is responsible for expelling the other materials from the container and forming the hairspray character.

The propellant gas can be any liquefiable gas conventionally used for aerosol containers. Preferably the density of the propellant or mixture thereof is less than so that pure propellant is not emitted from the container. Examples of materials that are suitable for use as propellants are trichlorofluoromethane, dichlorodifluoromethane, dichlorotetrafluoroethane, monochlorodifluoromethane, trichlorotrifluoroethane, dimethylether, propane, n-butane and isobutane, used singly or admixed. The hydrocarbons, particularly isobutane, used singly or admixed with other hydrocarbons are preferred due to their densities being less than 1.

The amount of the propellant gas is governed by normal factors well known in the aerosol art. For hairsprays the level of propellant is generally from about 3% to about 30%, preferably from about 5% to about 15% of the total composition. If a propellant such as dimethylether utilizes a vapor pressure suppressant (e.g., trichloroethane or dichloromethane) the amount of suppressant is included as part of the propellant.

The hair spray compositions herein can contain other optional components suitable for rendering such compositions more acceptable. Such conventional optional ingredients are well known to those skilled in the art and include such things as fragrances, sunscreens and proteins. As with all compositions, the present compositions should not contain components which unduly interfere with the performance of the compositions.

The pH of the present compositions is between about 3 and about 7, preferably between about 4 and about 6.

METHOD OF MAKING

The hair spray compositions of the present invention can be made using any conventional formulations and mixing techniques. If a volatile silicone carrier is used in the compositions of the present invention to lower the viscosity of the silicone gum, it is preferably combined with the silicone gum in several steps. The dispersing aid (surfactant emulsifier or hydrophobically-modified clay) is preferably premixed with the silicone gum or silicone gum/volatile silicone carrier mixture prior to combination with the other hairspray components. Methods of making hair spray compositions of the present invention are described more specifically in the following examples.

METHOD OF USE

The hair spray compositions of the present invention are used in conventional ways to provide the hair conditioning/styling/ holding benefits of the present invention. Such method generally involves application of an effective amount of the product to dry and/or slightly damp hair before and/or after the hair is styled. By "effective amount" is meant an amount sufficient to provide the hair volume and style benefits desired considering the length and texture of the hair. Use of the compositions of the present invention in this manner provides optimum hair holding, and volumizing benefits, while at the same time leaving the hair with a softer feel and more manageability than traditional hairspray products provide.

The following Examples further illustrate the preferred embodiments within the scope of the present invention. The Examples are given solely for the purposes of illustration and are not to be construed as limitations of the present invention as many variations of the invention are possible without departing from its spirit and scope.

EXAMPLE I
Non-Aerosol Silicone Hairspray

| Component | Weight % |
|---|---|
| Ethanol (190 proof) | 87.439 |
| PVP/VA copolymer (50/50) | 10.00 |
| Cyclomethicone[1] | 1.60 |
| Dimethicone copolyol[2] | 0.50 |
| Tixogel VP[3] | 0.10 |
| Polydimethylsiloxane gum[4] | 0.20 |
| Octyl Salicylate | 0.01 |
| Keratin Amino Acids | 0.001 |
| Fragrance | 0.10 |
| | 100% |

[1] Cyclomethicone having a D5 structure available from GE Silicones
[2] FF400 Dimethicone Copolyol available from Dow Corning
[3] Quaternium 18-Bentonite available from United Catalysts
[4] SE-30 Gum available from GE Silicones The polydimethylsiloxane gum is added to the cyclomethicone and mixed until dissolved using a dough style mixer for about 8 hours. The dimethicone copolyol is added and the composition mixed using the dough style mixer until homogeneous. The Tixogel ® is then added and mixed using the dough style mixer until homogeneous. Using a Tek Mar ® mill the composition is slowly milled with the ethanol until homogeneous. Using conventional mixing the PVP/VA copolymer is added. The octyl salicylate, keratin amino acids, and fragrance are mixed into the composition in that order.

The hairspray composition should be shaken well before each use to redisperse the silicone gum.

The resulting hairspray provides improved hair conditioning and volumizing benefits with a softer feeling hair hold.

Substantially similar results are obtained when an equivalent amount of a quaternium-18-hectorite (for example, the material sold under the tradename Bentone-38 ® by NL Chemicals); a stearalkonium bentonite (for example, the material sold under the trade name Tixogel VZ ® by United Catalysts) or a stearalkonium hectorite (for example, the material sold under the tradename Bentone-27 ® by NL Chemicals), is substituted for the Tixogel VP ® clay.

An aerosol silicone hairspray can be prepared by combining the composition described above with a propellant, for example, A-31 propellant, which is an isobutane propellant, available from Phillips Petroleum Company, at a ratio of 3 parts hairspray composition to 1 part propellant.

Example II
Aerosol Silicone Hairspray

| Component | Weight % |
| --- | --- |
| A-31 Propellant[1] | 75.00 |
| Ethanol 190-proof | 22.00 |
| Polydimethyl siloxane[2] | 2.50 |
| Silica[3] | 0.50 |
| Cyclomethicone[4] | 1.50 |
| Bentone-27[5] | 0.10 |
| PVP/VA copolymer (50/50) | 10.00 |
| Fragrance | 0.10 |
|  | 100% |

[1]Isobutane available from Phillips Petroleum Co.
[2]SE-76 gum, available from General Electric Co.
[3]Cab-O-Sil HS-5, available from Cabot Corp.
[4]Cyclomethicone having a D5 structure available from GE Silicones
[5]Stearalkonium hectorite available from NL Chemicals The polydimethyl siloxane and silica are intimately mixed in a high shear ribbon mixer for at least 4 hours. The gum mixture is then added to the cyclomethicone and mixed until dissolved using a dough style mixer for about 8 hours. The Bentone 27 ® is then added and mixed using the dough style mixer until homogeneous. A Tek Mar ® mill is then used to mill the composition with the ethanol until the composition is homogeneous. The PVP/VA copolymer and fragrance are added using conventional mixing.

| Component | Weight % |
| --- | --- |
| Example III Silicone Hairspray Composition | |
| SD40 Alcohol | 87.29 |
| Premix 1 | 2.30 |
| PVP/VA copolymer (50/50) | 10.00 |
| Dimethicone Copolyol[1] | 0.30 |
| Octyl Salicylate | 0.01 |
| Keratin Amino Acids | 0.001 |
| Perfume | 0.01 |
|  | 100% |
| Premix 1 | |
| D5 Cyclomethicone[2] | 4.35 |
| Siloxane Resin[3] | 4.35 |
| Polydimethyl Siloxane Gum[4] | 1.74 |
| DRO Water | 11.30 |
| Lauramine Oxide | 43.48 |
| Cocamide DEA | 34.78 |
| | 100% |

[1]FF400 Dimethicone Copolyol available from Dow Corning
[2]Cyclomethicone having a D5 structure available from GE Silicones
[3]GE SR545 available from GE Silicones
[4]SE-76 gum available from General Electric Co.

The polydimethyl siloxane gum is added to the cyclomethicone and siloxane resin and mixed until dissolved using a dough style mixer for about 8 hours. The DRO water is added and mixed until homogeneous. The lauramine oxide is added and mixed until homogeneous. The cocamide DEA is added and mixed until homogeneous. The SD40 alcohol is milled with the premix until homogeneous. The PVP/VA copolymer, dimethicone copolyol, octyl salicylate, keratin amino acids, and perfume are then each in turn mixed into the composition.

The result is a stable microemulsion of the silicone gum in the hairspray composition.

What is claimed is:

1. A hair spray composition comprising:
   (a) from about 0.05% to about 10.0% by weight of the composition of a silicone gum;
   (b) from about 0.05% to about 7.5% by weight of the composition of a dispersing aid wherein said dispersing and is a surfactant emulsifier or a hydrophobically-modified, quaternary ammonium treated montmorillonite clay or mixtures thereof for the silicone gum; and
   (c) from about 20% to about 95% of a volatile carrier.

2. The composition of claim 1 wherein the viscosity of the silicone gum is from about 100,000 centistoke to about 300,000,000 centistoke.

3. The composition of claim 2 wherein the silicone gum is polydimethyl siloxane gum having a viscosity of from about 1,000,000 centistoke to about 20,000,000 centistoke.

4. The composition of claim 1 wherein the silicone gum has a complex viscosity of at least $2 \times 10^5$ poise.

5. The composition of claim 4 wherein the silicone gum is selected from the group consisting of organic substituted siloxane gums, silicone elastomers, filler reinforced polydimethyl siloxane gums, resin reinforced siloxanes, and crosslinked siloxane polymers.

6. The composition of claim 5 wherein the silicone gum has a complex viscosity of at least $1 \times 10^7$ poise.

7. The composition of claim 6 wherein the silicone gum is a silicone elastomer.

8. The composition of claim 6 wherein the silicone gum is a filler reinforced polydimethyl siloxane gum.

9. The composition of claim 8 wherein the filler material is silica.

10. The composition of claim 6 wherein the silicone gum is an organic substituted siloxane gum.

11. The composition of claim 6 wherein the silicone gum is a resin reinforced siloxane.

12. The composition of claim 1 which additionally comprises from about 0.01% to about 10% of a volatile silicone solvent for the silicone gum.

13. The composition of claim 12 wherein the volatile silicone solvent is a cyclic silicone containing from about 3 to about 7 silicon atoms.

14. The composition of claim 13 wherein the volatile silicone solvent is cyclomethicone and is present at a level of from about 0.05% to about 5.0% of the composition.

15. The composition of claim 1 wherein the dispersing aid is a quaternary ammonium treated montmorillonite clay or mixtures thereof hydrophobically-modified clay, and is present in the composition at a level of from about 0.05% to about 5.0%.

16. The composition of claim 15 wherein the hydrophobically modified clay agent comprises from about 0.05% to about 2.0% of the composition.

17. The composition of claim 16 wherein the hydrophobically-modified clay agent is selected from the group consisting of hydrophobically-modified hectorite, hydrophobically-modified bentonite and mixtures thereof.

18. The composition of claim 17 wherein the hydrophobically modified clay agent is selected from the group consisting of quaternium-18-bentonite, quaternium-18-hectorite, stearalkonium bentonite, stearalkonium hectorite, and mixtures thereof.

19. The composition of claim 1 wherein the dispersing agent is a surfactant emulsifier and is present in the composition at a level of from about 0.25% to about 7.5%.

20. The composition of claim 19 wherein the surfactant emulsifier is a material which will allow for the formation of a microemulsion of the silicone gum in the hairspray composition.

21. The composition of claim 20 wherein the surfactant emulsifier is selected from the group consisting of anionic, cationic, nonionic surfactants and mixtures thereof.

22. The composition of claim 21 wherein the surfactant emulsifier is selected from the group consisting of a combination of anionic and nonionic surfactants and a combination of cationic and nonionic surfactants.

23. The composition of claim 22 wherein the surfactant emulsifier comprises a combination of lauramine oxide and cocamide DEA.

24. The composition of claim 1 wherein the volatile carrier is selected from the group consisting of $C_1-C_6$ alkanols.

25. The composition of claim 24 wherein the volatile carrier is ethanol.

26. The composition of claim 1 additionally comprising from about 0.25% to about 20% of a hair-holding resin selected from the group consisting of poly vinyl/pyrrolidone, copolymers of poly vinyl pyrrolidone and methylmethacrylate, copolymers of poly vinyl pyrrolidone and vinylacetate, polyvinyl alcohol, copolymers of polyvinyl alcohol and crotonic acid, copolymers of polyvinyl alcohol and maleic anhydride, hydroxy propyl cellulose, hydroxypropyl guar gum, sodium polystyrene sulfonate, polyvinyl pyrrolidone/ethylmethacrylate/methacrylic acid terpolymer, vinyl acetate/crotonic acid/vinyl neodecanoate copolymer, octylacrylamide/acrylates copolymer, monoethyl ester of poly(methyl vinyl ether-maleic acid), octyl, acrylamide/acrylate/butylaminoethyl methacrylate copolymers and mixtures thereof; which is solubilized in the volatile carrier.

27. The composition of claim 26 wherein the hair holding resin comprises from about 1% to about 20% of a copolymer of polyvinyl pyrrolidone and vinyl acetate.

28. The composition of claim 1 in aerosol form additionally comprising from about 3% to about 30% of a propellant.

29. The composition of claim 28 wherein the propellant is selected from the group consisting of trichlorofluoromethane, dichlorodifluoromethane, dichlorotetrafluoroethane, monochlorodifluoromethane, trichlorotrifluoroethane, dimethylether, propane, n-butane, isobutane and mixtures thereof.

30. A hairspray composition comprising:
(a) from about 0.05% to about 7.0% by weight of the composition, of a polydimethyl siloxane gum having a viscosity of from about 1,000,000 centistoke to about 20,000,000 centistoke;
(b) from about 0.05% to about 5.0% of a volatile silicone solvent for the polydimethyl siloxane gum;
(c) from about 0.05% to about 2.0% by weight of the composition of a hydrophobically modified clay agent selected from the group consisting of a quaternium-18-bentonite, quaternium-18-hectorite, stearalkonium bentonite, stearalkonium hectorite, and mixtures thereof;
(d) from about 1% to about 20% of a hair-holding resin which is selected from the group consisting of poly vinyl/pyrrolidone, copolymers of poly vinyl pyrrolidone and methylmethacrylate, copolymers of poly Vinyl pyrrolidone and vinylacetate, polyvinyl alcohol, copolymers of polyvinyl alcohol and crotonic acid, copolymers of polyvinyl alcohol and maleic anhydride, hydroxy propyl cellulose, hydroxypropyl guar gum, sodium polystyrene sulfonate, polyvinyl pyrrolidone/ethylmethacrylate/methcarylic acid terpolymer, vinyl acetate/crotonic acid/vinyl neodecanoate copolymer, octylacrylamide/acrylates copolymer, monoethyl ester of poly (methyl vinyl ether-maleic acid), octyl acrylamide/acrylate/ butylaminoethyl methacrylate copolymers and mixtures thereof; which is solubilized in the volatile carrier; and
(e) from about 35% to about 95% of ethanol.

31. A hairspray composition comprising:
(a) from about 0.05% to about 7.0% by weight of the composition, of a polydimethyl siloxane gum having a viscosity of from about 1,000,000 centistoke to about 20,000,000 centistoke;
(b) from about 0.05% to about 5.0% of a volatile silicone solvent for the polydimethyl siloxane gum;
(c) from about 0.25% to about 7.5% by weight of the composition of a surfactant emulsifier which is a combination of lauramine oxide and cocamide DEA;
(d) from about 1% to about 20% of a hair-holding resin which is selected from the group consisting of poly vinyl/pyrrolidone, copolymers of poly vinyl pyrrolidone and methylmethacrylate, copolymers of poly vinyl pyrrolidone and vinylacetate, polyvinyl alcohol, copolymers of polyvinyl alcohol and crotonic acid, copolymers of polyvinyl alcohol and maleic anhydride, hydroxy propyl cellulose, hydroxypropyl guar gum, sodium polystyrene sulfonate, polyvinyl pyrrolidone/ethylmethacrylate/methacrylic acid terpolymer, vinyl acetate/crotonic acid/vinyl neodecanoate copolymer, octylacrylamide/acrylates copolymer, monoethyl ester of poly (methyl vinyl ether-maleic acid), octyl acrylamide/acrylate/ butylaminoethyl methacrylate copolymers and mixtures thereof; which is solubilized in the volatile carrier; and
(e) from about 35% to about 95% of ethanol.

32. A hairspray composition comprising:
(a) from about 0.05% to about 7.0% by weight of the composition, of a silicone gum, having a complex viscosity of at least about $2 \times 10^5$ poise; selected from the group consisting of organic substituted siloxane gums, silicone elastomers, filler reinforced polydimethyl siloxane gums, resin reinforced siloxanes, and crosslinked siloxane polymers;

(b) from about 0.05% to about 5.0% of a volatile silicone solvent for the polydimethyl siloxane gum;

(c) from about 0.05% to about 2.0% by weight of the composition of a hydrophobically modified clay agent selected from the group consisting of a quaternium-18-bentonite, quaternium-18-hectorite, stearalkonium bentonite, stearalkonium hectorite, and mixtures thereof;

(d) from about 1% to about 20% of a hair-holding resin which is selected from the group consisting of poly vinyl/pyrrolidone, copolymers of poly vinyl pyrrolidone and methylmethacrylate, copolymers of poly vinyl pyrrolidone and vinylacetate, polyvinyl alcohol, copolymers of polyvinyl alcohol and crotonic acid, copolymers of polyvinyl alcohol and maleic anhydride, hydroxy propyl cellulose, hydroxypropyl guar gum, sodium polystyrene sulfonate, polyvinyl pyrrolidone/ethylmethacrylate/methacrylic acid terpolymer, vinyl z5 acetate/crotonic acid/vinyl neodecanoate copolymer, octylacrylamide/acrylates copolymer, monoethyl ester of poly (methyl vinyl ether maleic acid), octyl acrylamide/acrylate/ butylaminoethyl methacrylate copolymers and mixtures thereof; which is solubilized in the volatile carrier; and (e) from about 35% to about 95% of ethanol.

33. A hairspray composition comprising:

(a) from about 0.05% to about 7.0% by weight of the composition, of a silicone gum, having a complex viscosity of at least about $2 \times 10^5$ poise, selected from the group consisting of organic substituted siloxane gums, silicone elastomers, filler reinforced polydimethyl siloxane gums, resin reinforced siloxanes, and crosslinked siloxane polymers;

(b) from about 0.05% to about 5.0% of a volatile silicone solvent for the siloxane gum;

(c) from about 0.25% to about 7.5% by weight of the composition of a surfactant emulsifier which is a combination of lauramine oxide and cocamide DEA;

(d) from about 1% to about 20% of a hair-holding resin which is selected from the group consisting of poly vinyl/pyrrolidone, copolymers of poly vinyl pyrrolidone and methylmethacrylate, copolymers of poly vinyl pyrrolidone and vinylacetate, polyvinyl alcohol, copolymers of polyvinyl alcohol and crotonic acid, copolymers of polyvinyl alcohol and maleic anhydride, hydroxy propyl cellulose, hydroxypropyl guar gum, sodium polystyrene sulfonate, polyvinyl pyrrolidone/ethylmethacrylate/methacrylic acid terpolymer, vinyl acetate/crotonic acid/vinyl neodecanoate copolymer, octylacrylamide/acrylates copolymer, monoethyl ester of poly (methyl vinyl ether maleic acid), octyl acrylamide/acrylate/ butylaminoethyl methacrylate copolymers and mixtures thereof; which is solubilized in the volatile carrier; and (e) from about 35% to about 95% of ethanol.

* * * * *

UNITED STATES PATENT AND TRADEMARK OFFICE
CERTIFICATE OF CORRECTION

PATENT NO. : 4,983,418
DATED     : January 8, 1991
INVENTOR(S) : C.S. Murphy, et. al.

It is certified that error appears in the above-indentified patent and that said Letters Patent is hereby corrected as shown below:

Column 7, line 40 "than so" should read --than 1 so--

Column 12, line 21 "poly Vinyl" should read --poly vinyl--

Column 13, line 23 "vinyl z5 acetate/" should read --vinyl acetate/

Signed and Sealed this

Eleventh Day of February, 1997

Attest:

BRUCE LEHMAN

*Attesting Officer*     *Commissioner of Patents and Trademarks*